(12) United States Patent
Chen et al.

(10) Patent No.: US 7,923,590 B2
(45) Date of Patent: Apr. 12, 2011

(54) PRODUCTION OF ALKYLAROMATIC COMPOUNDS (75) Inventors: Shiou-Shan Chen, Winchester, MA (US); Shyh-Yuan H. Hwang, Newton, MA (US)

(73) Assignees: ExxonMobil Chemical Patents Inc, Houston, TX (US); Stone & Webster, Inc., Houston, TX (US)

( * ) Notice: Subject to any disclaimer, the term of this patent is extended or adjusted under 35 U.S.C. 154(b) by 173 days.

(21) Appl. No.: 12/163,446

(22) Filed: Jun. 27, 2008

(65) Prior Publication Data

US 2008/0262279 A1 Oct. 23, 2008

Related U.S. Application Data (62) Division of application No. 10/466,719, filed on Jul. 12, 2003, now Pat. No. 7,411,101.

(51) Int. Cl.
*C07C 2/66* (2006.01)

(52) U.S. Cl. ........ 585/467; 585/316; 585/315; 585/323; 585/447; 585/475

(58) Field of Classification Search .......... None
See application file for complete search history.

(56) References Cited

U.S. PATENT DOCUMENTS

| | | |
|---|---|---|
| 3,130,007 A | 4/1964 | Breck |
| 3,293,192 A | 12/1966 | Maher et al. |
| 3,308,069 A | 3/1967 | Wadlinger et al. |
| 3,442,795 A | 5/1969 | Kerr et al. |
| 3,449,070 A | 6/1969 | McDaniel et al. |
| 3,702,886 A | 11/1972 | Argauer et al. |
| 3,751,504 A | 8/1973 | Keown et al. |
| 3,755,483 A | 8/1973 | Burress |
| 3,832,449 A | 8/1974 | Rosinski et al. |
| RE28,341 E | 2/1975 | Wadlinger et al. |
| 4,016,218 A | 4/1977 | Haag et al. |
| RE29,948 E | 3/1979 | Dwyer et al. |
| 4,169,111 A | 9/1979 | Wight |
| 4,439,409 A | 3/1984 | Puppe et al. |
| 4,459,426 A | 7/1984 | Inwood et al. |
| 4,547,605 A | 10/1985 | Kresge et al. |
| 4,891,458 A | 1/1990 | Innes et al. |
| 4,954,325 A | 9/1990 | Rubin et al. |
| 4,992,606 A | 2/1991 | Kushnerick et al. |
| 5,003,119 A | 3/1991 | Sardina et al. |
| 5,077,445 A | 12/1991 | Le |
| 5,236,575 A | 8/1993 | Bennett et al. |
| 5,250,277 A | 10/1993 | Kresge et al. |
| 5,258,565 A | 11/1993 | Kresge et al. |
| 5,292,698 A | 3/1994 | Chu et al. |
| 5,334,795 A | 8/1994 | Chu et al. |
| 5,362,697 A | 11/1994 | Fung et al. |
| 5,371,310 A | 12/1994 | Bennett et al. |
| 5,437,855 A | 8/1995 | Valyocsik |
| 5,453,554 A | 9/1995 | Cheng et al. |
| 5,493,065 A | 2/1996 | Cheng et al. |
| 5,557,024 A | 9/1996 | Cheng et al. |
| 5,563,311 A | 10/1996 | Chang et al. |
| 5,569,805 A | 10/1996 | Beck et al. |
| 5,866,738 A | 2/1999 | Bencini et al. |
| 5,902,917 A | 5/1999 | Collins et al. |

(Continued)

*Primary Examiner* — Tam M Nguyen
(74) *Attorney, Agent, or Firm* — Darryl M. Tyus (57) ABSTRACT A process for producing a monoalkylation aromatic product, such as ethylbenzene and cumene, utilizing an alkylation reactor zone and a transalkylation zone in series or a combined alkylation and transalkylation reactor zone. This process requires significantly less total aromatics distillation and recycle as compared to the prior art.

11 Claims, 3 Drawing Sheets

U.S. PATENT DOCUMENTS

| | | |
|---|---|---|
| 6,005,152 A | 12/1999 | Amarilli et al. |
| 6,043,402 A | 3/2000 | Gajda |
| 6,049,018 A | 4/2000 | Calabro et al. |
| 6,051,521 A | 4/2000 | Cheng et al. |
| 6,096,935 A | 8/2000 | Schulz et al. |
| 6,297,417 B1 | 10/2001 | Samson et al. |
| 6,479,721 B1 * | 11/2002 | Gajda et al. .......... 585/467 |
| 6,747,182 B2 | 6/2004 | Timken et al. |

* cited by examiner

PRODUCTION OF ALKYLAROMATIC COMPOUNDS

This application is a divisional of U.S. application Ser. No. 10/466,719 filed Jul. 17, 2003, now U.S. Pat. No. 7,411,101, which claims priority to PCT/US02/03801, filed Feb. 6, 2002 which claims priority to U.S. Provisional Application No. 60/267,035 filed Feb. 7, 2001 and is fully incorporated herein by reference.

The present invention relates generally to improvements in the production of alkyl aromatic compounds, particularly cumene and ethylbenzene, utilizing alkylation and transalkylation in novel series or combination configurations to achieve significant improvements in process efficiencies.

BACKGROUND OF THE INVENTION

Cumene and Cumene Production

Cumene is an aromatic compound. It is a clear liquid at ambient conditions. High purity cumene is conventionally manufactured from propylene and benzene. Cumene is used today primarily as a feed in manufacturing the products phenol and acetone, which are two important petrochemicals with many uses in the chemical and polymer industries. Global cumene production in 1998 was about 7 million metric tons.

Cumene was first synthesized in large quantities during World War II as an aviation gasoline. It has a high heating value and a high octane number, but it is not economically competitive today as a fuel. Its presence in gasoline is now incidental, being an inevitable minor reaction product of refinery processes such as catalytic reforming and steam cracking.

Production of cumene was considered a rather conventional and routine business for many years, but recently has generated considerable excitement for two reasons. First, the demand for phenol for manufacturing polycarbonates is accelerating rapidly owing to the broadening applications of polycarbonates in the electronic, healthcare, and automobile industries. Second, successful development and commercialization of the zeolite-based alkylation technology for the isopropylation of benzene to cumene has rendered obsolete the older processes which were based on solid phosphoric acid and aluminum chloride. Within a period of just over two years during 1996-98, over one half of the cumene capacity in the world was converted to the new zeolite technologies.

Figure 1:
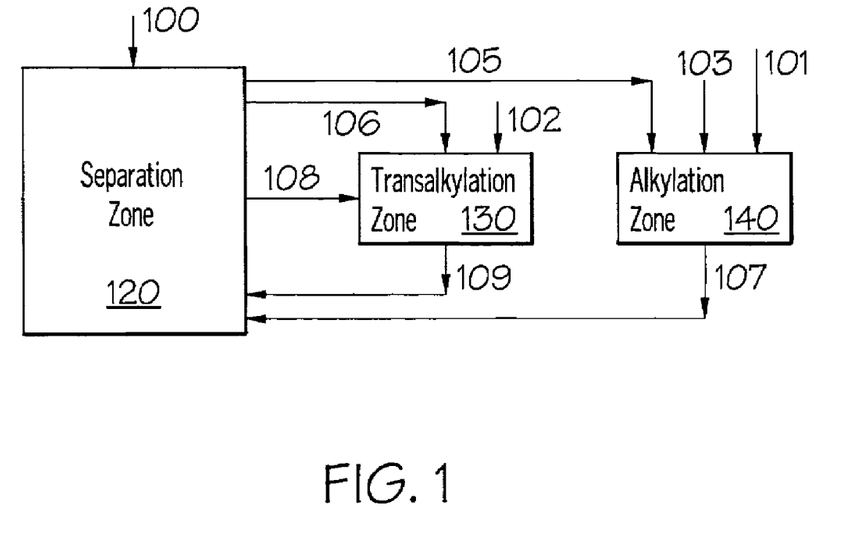
FIG. 1 is a schematic representation of a first prior art process, as discussed above, for the production of alkylaromatic compounds in which separate alkylation and transalkylation reactors are configured in a conventional parallel mode.

New zeolite-based cumene technologies developed by Mobil/Badger, Dow/Kellogg, and UOP carry out the alkylation of benzene and propylene in liquid phase in the presence of a solid acidic zeolite catalyst. A process developed by CDTech achieves the alkylation of benzene and propylene in mixed phases in a catalytic distillation column packed with both distillation devices and bales of zeolite catalysts. FIG. 1 is a simplified representation of the zeolite-based cumene technologies. All of these zeolite-based cumene technologies utilize a separate transalkylation zone which is operated in parallel with the alkylation zone, to react a mixture of benzene and the polyisopropylbenzene alkylation byproducts to form additional cumene in liquid phase in the presence of a solid acidic catalyst. A separation zone is utilized to recover the unreacted benzene and polyisopropylbenzenes for recycle, and to isolate the desired cumene product.

Ethylbenzene and Ethylbenzene Production

Ethylbenzene is a commodity chemical currently used mostly for the production of styrene. Global ethylbenzene production in 1998 was about 19 million metric tons. Ethylbenzene may be prepared by a number of different chemical processes, but present commercial ethylbenzene production is dominated by zeolite-based technologies. The first zeolite-based ethylbenzene process, developed jointly by Mobil and Badger in the early 1980s, utilizes a combination of vapor phase alkylation of benzene with ethylene and vapor phase trans-alkylation of a benzene and polyethylbenzene mixture. Both the alkylation and transalkylation steps are carried out in the presence of solid acidic ZSM-5 catalysts.

Several liquid-phase zeolite-based ethylbenzene technologies were developed in the late 1980s and in the 1990s by UOP/Lummus and Mobil/Badger. Alkylation of benzene with ethylene and transalkylation of mixtures of benzene and polyethylbenzenes are carried out in liquid phase in the presence of solid acidic zeolite catalysts. Catalysts that can be used for alkylation of benzene with ethylene and for transalkylation of benzene and polyethylbenzenes in at least partial liquid phase include zeolite beta, zeolite Y, ZSM-5, PSH-3, ITQ-2, ZSM-12, MCM-22, MCM-36, MCM-49, MCM-56, MCM-58, MCM-68, faujasite, mordenite, porous crystalline magnesium silicates, and tungstate modified zirconia.

Processes for the production of ethylbenzene over intermediate-pore size zeolites are described in U.S. Pat. Nos. 3,751,504 (Keown); 4,547,605 (Kresge); and 4,016,218 (Haag). U.S. Pat. Nos. 4,169,111 (Wight) and 4,459,426 (Inwood) disclose production of ethylbenzene over large-pore size zeolites such as zeolite Y. A process for ethylbenzene production over zeolite ZSM-12 is described in U.S. Pat. No. 3,755,483 (Burress). Liquid phase synthesis of ethylbenzene with zeolite beta is described in U.S. Pat. No. 4,891,458.

To minimize the formation of polyalkylaromatics and other undesired impurities (e.g., oligomers of the olefin), production of alkylaromatics such as ethylbenzene and cumene typically operates with relatively high (excess) mole ratios of aromatic (e.g., benzene) to olefin (e.g., ethylene or propylene) in the alkylation reactor feed. Zeolite-based alkylaromatic processes generally operate at aromatic to olefin feed molar ratios of three or above, while aluminum chloride-based processes often operate at aromatic to olefin molar ratios of three and below. In both cases, however, the polyalkylaromatics are produced at sufficiently high levels that it would be prohibitively expensive to simply dispose of them as low value byproducts. Instead, these polyalkylated aromatics are typically reacted further with feed aromatic to form additional monoalkylate via transalkylation reactions.

In the case of the Mobil/Badger vapor phase ethylbenzene process mentioned above, the transalkylation reaction may take place in the alkylation reactor or in a separate transalkylation reactor. U.S. Pat. Nos. 5,902,917 (Collins) and 6,096,935 (Schulz) describe processes for the production of alkylaromatics wherein a feedstock is first fed to a transalkylation zone and the entire effluent from the transalkylation zone is then cascaded directly into an alkylation zone along with an olefin alkylating agent.

Conventionally, relatively high molar ratios of aromatic (e.g., benzene) to olefin (e.g., ethylene or propylene) have been used successfully commercially in the production of alkylaromatics (e.g., ethylbenzene or cumene) to minimize the formation of polyalkylaromatics and other undesired impurities (e.g., oligomers of the olefins). The disadvantage of using high molar ratios of aromatic to olefin, however, is that the recovery and the subsequent circulation (re-use) of the unreacted aromatics consumes very substantial amounts of energy which increases the production cost of the desired alkylaromatics.

The recovery and circulation of large amounts of unreacted aromatics also requires larger capacity separation equipment (usually distillation columns) and larger pumps, both of which increase capital cost of the plant, and thus also increase the cost of production.

It is therefore of crucial interest to minimize the amount of excess aromatics that is used and needs to be recovered and subsequently circulated in order to minimize the production cost. It is of even more importance today in the production of highly competitive commodity chemicals (e.g., ethylbenzene and cumene) which are produced and traded globally, and at a time when the energy costs are high. Low aromatics circulation results in lower energy consumption, lower capital investment and thus a more efficient plant. This in turn enables a producer to establish itself as a low cost producer in a favorable (competitive) marketing position.

Because of these disadvantages and limitations of the prior art processes, it is desired to provide improved processes and apparatus for the production of alkylaromatic compounds. In this invention, two reaction configurations are provided which have been found to significantly reduce the total aromatic circulation, compared with prior art processes, at all aromatic to olefin ratios.

OBJECTS OF THE INVENTION

Accordingly, a general object of this invention is to provide improved processes and apparatus for the production of alkylaromatic compounds, particularly cumene and ethylbenzene.

More specifically, it is a principal object of this invention to provide processes and apparatus for the production of alkylaromatic compounds using less circulation of aromatics than in conventional processes.

It is a further principal object of this invention to provide processes and apparatus for the production of alkylaromatic compounds which use relatively low circulation of aromatics without increasing the production of unwanted byproducts, specifically polyalkylaromatics.

A specific object of this invention is to provide processes and apparatus for the production of alkylaromatic compounds which utilize in combination a reaction zone or step, broadly comprising alkylation and transalkylation, together with a separation zone or step.

Another specific object of this invention is to provide a reaction zone for the production of alkylaromatic compounds comprising an alkylation unit and a transalkylation unit in a particular series configuration.

Still another specific object of this invention is to provide a reaction zone for the production of alkylaromatic compounds comprising a combined alkylation-transalkylation unit.

Yet a further specific object of this invention is to prepare alkylaromatic compounds, such as cumene and ethylbenzene, utilizing the processes and apparatus described herein.

Other objects and advantages of the present invention will in part be obvious and will in part appear hereinafter. The invention accordingly comprises, but is not limited to, the processes and related apparatus, involving the several steps and the various components, and the relation and order of one or more such steps and components with respect to each of the others, as exemplified by the following description and the accompanying drawings. Various modifications of and variations on the processes and apparatus as herein described will be apparent to those skilled in the art, and all such modifications and variations are considered within the scope of the invention.

SUMMARY OF THE INVENTION

The present invention relates generally to improvements in alkylation and transalkylation processes and apparatus in the production of alkylaromatic compounds, for example cumene and ethylbenzene, utilizing a reaction section and a separation section. In accordance with the present invention, two novel alternative reactor configurations are provided for the reaction section. The two reaction section configurations provided in this invention share certain important commonalities including that both of these novel configurations require significantly less total aromatics distillation and circulation (recycle) than do the conventional configurations of both parallel alkylation/transalkylation reactors and the transalkylator-alkylator cascaded configuration described in U.S. Pat. Nos. 5,902,917 (Collins) and 6,096,935 (Schulz), even when operated at the same alkylator feed aromatics to olefin molar ratio, thereby reducing the capital and utility costs of producing the desired alkylaromatics.

In a first embodiment of the improved alkylaromatic production processes and apparatus according to this invention, the reaction section comprises an alkylation zone and a transalkylation zone configured to operate in a novel series arrangement. In this first embodiment, two or more separate feeds respectively consisting essentially of fresh and recycle aromatics and fresh olefin, or one or more at least partially combined feeds of aromatics and/or olefin, are sent to an alkylation zone where the aromatics and olefin are reacted in the presence of an alkylation catalyst in the alkylation zone. The effluent from the alkylation zone is sent to a transalkylation zone together with recycled polyalkylaromatics for the production of additional alkylaromatics. The alkylation and the transalkylation zones can be housed in the same vessel or in different vessels.

The alkylation is carried out substantially adiabatically in at least partial liquid phase, at temperatures between about 150° F. (66° C.) and 900° F. (482° C.) and at pressures between about 150 psig (1034 kPAg) and 2000 psig (13788 kPAg), over one or more beds of suitable alkylation catalyst(s) consisting essentially of at least one solid acid oxide selected from the group consisting of: zeolite beta, zeolite Y, ZSM-5, PSH-3, ITQ-2, ZSM-12, MCM-22, MCM-36, MCM-49, MCM-56, MCM-58, MCM-68, faujasite, mordenite, porous crystalline magnesium silicates, and tungstate modified zirconia. The overall molar ratio of aromatics to olefin fed to the alkylation zone is between about 1:1 and 20:1. The olefin fed to the alkylation zone is essentially completely reacted with the aromatics feed. The alkylation zone can be housed in one or more vessels.

The transalkylation is carried out substantially adiabatically in at least partial liquid phase, at temperatures between about 150° F. (66° C.) and 900° F. (482° C.) and at pressures between about 150 psig (1034 kPAg) and 2000 psig (13788 kPAg), over one or more beds of suitable transalkylation catalyst(s) consisting essentially of at least one solid acid oxide selected from the group consisting of: zeolite beta, zeolite Y, ZSM-5, PSH-3, ITQ-2, ZSM-12, MCM-22, MCM-36, MCM-49, MCM-56, MCM-58, MCM-68, faujasite, mordenite, porous crystalline magnesium silicates, and tungstate modified zirconia. The overall weight ratio of aromatics to polyaromatics fed to the transalkylation zone is between about 0.2:1 and 20:1. The transalkylation zone can be housed either in one or more separate vessels or, alternatively, in the same vessel or vessels where the alkylation zone is housed.

This process and apparatus may further comprise a separation zone wherein unreacted aromatic and polyalkylaromatic compounds are recovered and recycled, and the desired alkylaromatic product, for example cumene or ethylbenzene, is isolated.

In a second embodiment of the improved alkylaromatic production processes and apparatus according to this invention, the reaction section comprises a novel combined alkylation-transalkylation zone. In this second embodiment, three or more separate feeds respectively consisting essentially of fresh and recycle aromatics, fresh olefin, and recycled polyalkylaromatics, or one or more at least partially combined feeds of aromatics, olefin, and/or polyalkylaromatics, are sent to a combined alkylation-transalkylation zone where the components are reacted in the presence of catalyst. The effluent from the combined reaction zone is sent to a separation zone where unreacted aromatics and polyalkylaromatics are recovered and recycled, and the desired alkylaromatic product, for example cumene or ethylbenzene, is isolated.

The reaction is carried out substantially adiabatically in at least partial liquid phase, at temperatures between about 150° F. (66° C.) and 900° F. (482° C.) and at pressures between about 150 (1034 kPAg) and 2000 psig (13788 kPAg), over one or more beds of suitable alkylation-transalkylation catalyst(s) comprising at least one solid acid oxide selected from the group consisting of: zeolite beta, zeolite Y, ZSM-5, PSH-3, ITQ-2, ZSM-12, MCM-22, MCM-36, MCM-49, MCM-56, MCM-58, MCM-68, faujasite, mordenite, porous crystalline magnesium silicates, and tungstate modified zirconia. In this environment, it has been found that the reaction of aromatics and olefin to produce the monoalkylaromatics and polyalkylaromatics, and the reaction of aromatics and polyalkylaromatics to produce additional monoalkylaromatics, take place simultaneously over at least one catalyst bed.

The combined alkylation-transalkylation reaction zone can be housed in one or more vessels. The overall molar ratio of aromatics to olefin fed to the combined reaction zone is between about 1:1 and 20:1. The olefin fed to the combined reaction zone is essentially completely reacted. The overall weight ratio of aromatics to polyalkylaromatics fed to the combined reaction zone is between about 0.2:1 and 20:1.

DETAILED DESCRIPTION OF PREFERRED EMBODIMENTS

The novelty of the present invention can best be understood by comparison with and contrast to two important prior art approaches to producing alkylaromatic compounds.

A first familiar conventional approach to the production of alkylaromatic compounds, wherein separate alkylation and transalkylation reactors are used and operated in parallel mode, is illustrated schematically in FIG. 1. As shown in FIG. 1, the fresh aromatics feed can enter the process via line 100 to the separation zone 120, via line 101 into the alkylation zone 140, or via line 102 into the transalkylation zone 130. Part of the aromatic feed recovered from the separation zone 120 is sent to the alkylation zone 140 via line 105. A second part of the aromatic feed recovered in the separation zone 120 is sent to the transalkylation zone 130 via line 106. Fresh olefin feed is introduced into the alkylation zone 140 via line 103, and the effluent from the alkylation zone 140 is sent to the separation zone 120 via line 107. The polyalkylaromatics product recovered in the separation zone 120 is sent to the transalkylator 130 via line 108. The effluent from the transalkylation zone 130 is sent to the separation zone 120 via line 109.

Figure 2:
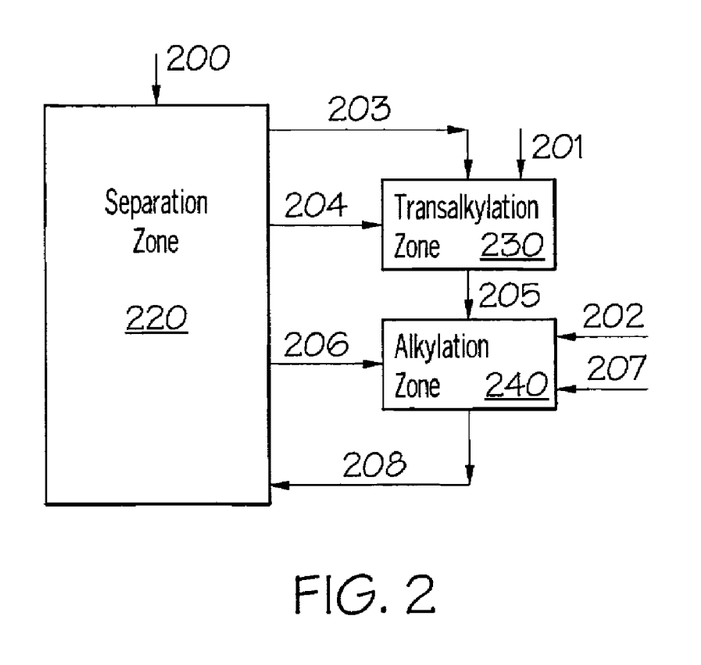
FIG. 2 is a schematic representation of a second prior art process, as discussed above, for the production of alkylaromatic compounds, a cascaded configuration in which the entire effluent from the transalkylation zone is cascaded directly into an alkylation zone along with an olefin.

A second familiar conventional approach to the production of alkylaromatic compounds, utilizing a cascaded process as described in U.S. Pat. Nos. 5,902,917 (Collins) and 6,096,935 (Schulz), is illustrated schematically in FIG. 2. As shown in FIG. 2, the fresh aromatics feed can enter the process either via line 200 to the separation zone 220, via line 201 to the transalkylation zone 230, or via line 202 into the alkylation zone 240. A first part of the aromatic feed recovered from the separation zone 220 is sent to the transalkylation zone 230 via line 203. A second part of the aromatic feed recovered from the separation section 220 is introduced into the alkylation zone 240 via line 206. The polyalkylaromatic product recovered from the separation zone 220 is sent to the transalkylation zone 230 via line 204. The effluent from the transalkylation zone 230 is sent to the alkylation zone 240 via line 205. The fresh olefin feed to the process is introduced into the alkylation zone 240 via line 207 whereas the effluent from the alkylation zone 240 is sent to the separation zone 220 via line 208.

Figure 3:
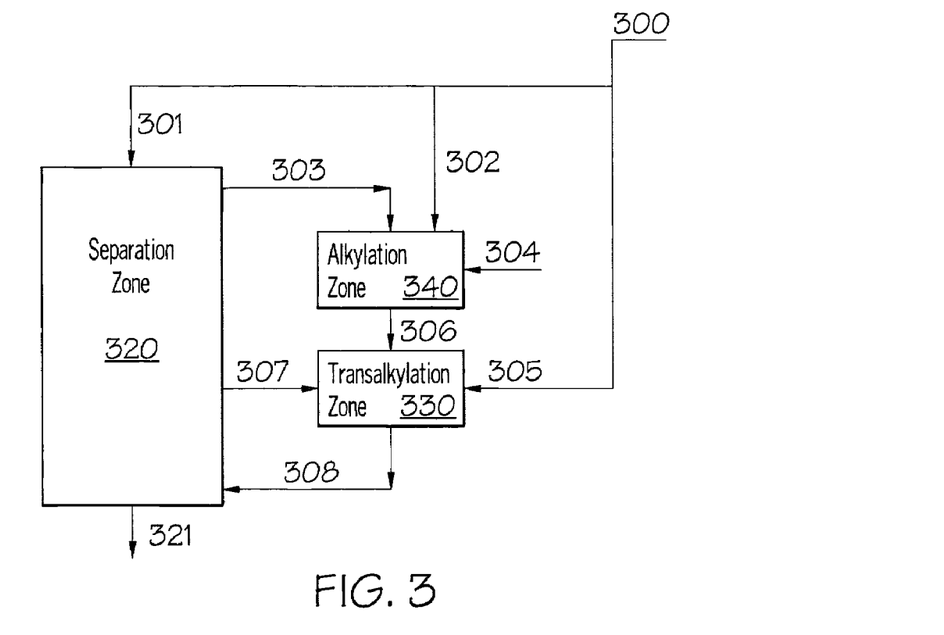
FIG. 3 is a schematic representation of a first embodiment of the present invention wherein the reaction section comprises an alkylation zone and a transalkylation zone configured to operate in series.

In contrast to the prior art configurations, a first embodiment of the present invention wherein the reaction section comprises an alkylation zone and a transalkylation zone configured to operate in series is illustrated schematically in FIG. 3. As shown in FIG. 3, the fresh aromatics feed 300 can enter the process either via line 301 into separation zone 320, via line 302 into the alkylation zone 340 or, alternatively, via line 305 into the transalkylation zone 330. The aromatic product recovered from separation zone 320 is introduced into the alkylation zone 340 via line 303, and the fresh olefin feed enters the process via line 304 into the alkylation zone 340. The effluent from the alkylation zone 340 is sent to the transalkylation zone 330 via line 306. The polyalkylaromatic product recovered in separation zone 320 is introduced into the transalkylation zone 330 via line 307. The effluent from the transalkylation zone 330 is sent to separation zone 320 via line 308. The monoalkylated product is removed from the separation zone 320 via line 321.

As seen in FIG. 3, the first embodiment of the present invention comprises the following process steps:

(a) introducing into an alkylation zone by two or more individual component feeds or one or more at least partly combined feeds, a reaction mixture comprising fresh and recycle aromatics and fresh olefin, wherein the molar ratio of aromatics to olefin in the mixture is in excess of 1:1, and also wherein the alkylation zone includes a suitable alkylation catalyst(s);

(b) contacting the aromatic/olefin mixture with the alkylation catalyst(s) under sufficient alkylation conditions to react essentially all the olefins in the mixture to monoalkylated aromatics and polyalkylated aromatics, to produce an effluent from the alkylation zone comprising monoalkylated and polyalkylated aromatics and the unreacted aromatics;

(c) introducing a feed into a transalkylation zone, the feed comprising the effluent from the alkylation zone, recycled polyalkylaromatics, and possibly additional aromatics, wherein the transalkylation zone includes a suitable transalkylation catalyst;

(d) contacting the feed to the transalkylation zone with the transalkylation catalyst under sufficient transalkylation conditions to react at least a part of the aromatics and the polyalkylated aromatics in the feed to additional monoalkylated aromatics to produce an effluent from the transalkylation zone comprising the desired mono-alkylated aromatics and the unreacted aromatics and polyalkylated aromatics; and, (e) introducing the transalkylation zone effluent into a separation zone wherein the desired monoalkylated aromatics product is isolated and recovered and the unreacted aromatics and polyalkylated aromatics are recovered and recycled.

The alkylation step of this first embodiment of the present invention may be carried out in at least partial liquid phase at temperatures between about 150° F. (66° C.) and 900° F. (482° C.) and at pressures between about 150 psig (1034 kPAg) and 2000 psig (13788 kPAg), over one or more beds of suitable alkylation catalyst(s) comprising at least one solid acid oxide selected from the group consisting of: zeolite beta, zeolite Y, ZSM-5, PSH-3, ITQ-2, ZSM-12, MCM-22, MCM-36, MCM-49, MCM-56, MCM-58, MCM-68, faujasite, mordenite, porous crystalline magnesium silicates, and tungstate modified zirconia. The overall molar ratio of aromatics to olefin fed to the alkylation zone may be between about 1:1 to 20:1. The olefin fed to the alkylation zone is essentially completely reacted with the aromatics feed. The alkylation zone can be housed in one or more vessels. Each alkylation vessel can have one or more catalyst beds containing the same or different alkylation catalysts or catalyst mixtures. Part of the total effluent from the alkylation zone may be recycled back to some or all of the alkylation catalyst beds, with or without cooling, for temperature control purposes.

Zeolite beta catalyst is described in U.S. Pat. No. 3,308,069 and Re. 28,341. Different versions of zeolite Y are described in U.S. Pat. Nos. 3,130,007; 3,293,192; 3,449,070; and 3,442,795. ZSM-5 is described in detail in U.S. Pat. Nos. 3,702,886 and Re. 29,948. ZSM-12 is described in U.S. Pat. No. 3,832,449. PSH-3 is disclosed in U.S. Pat. No. 4,439,409.

MCM-22 catalyst and its use to catalyze the synthesis of alkylaromatics are described in U.S. Pat. Nos. 4,954,325; 4,992,606; 5,077,445; and 5,334,795. MCM-36 and its use in the synthesis of alkylaromatics are described in U.S. Pat. Nos. 5,250,277; 5,292,698; and 5,258,565. MCM-49 and its use in the synthesis of alkylaromatics are described in U.S. Pat. Nos. 5,236,575; 5,493,065; and 5,371,310. MCM-56 and its use to catalyze the synthesis of alkylaromatics are described in U.S. Pat. Nos. 5,362,697; 5,453,554; 5,557,024; and 6,051,521. MCM-58 and its use for the production of alkylaromatics are described in U.S. Pat. Nos. 5,437,855 and 5,569,805. MCM-68 and its use for the production of alkylaromatics are described in U.S. Pat. No. 6,049,018. The use of tungstate modified zirconia to catalyze the synthesis of alkylaromatics is described in U.S. Pat. No. 5,563,311.

The transalkylation step of this first embodiment of the present invention is carried out in at least partial liquid phase at temperatures between about 150° F. and 900° F. and at pressures between about 150 and 2000 psig, over one or more beds of transalkylation catalyst(s) comprising at least one solid acid oxide selected from the group consisting of: zeolite beta, zeolite Y, ZSM-5, PSH-3, ITQ-2, ZSM-12, MCM-22, MCM-36, MCM-49, MCM-56, MCM-58, MCM-68, faujasite, mordenite, porous crystalline magnesium silicates, and tungstate modified zirconia. The overall weight ratio of aromatics to polyalkylaromatics fed to the transalkylation zone may be between about 0.2:1 and 20:1. The transalkylation zone can be housed either in one or more separate vessels or, alternatively, in the same vessel or vessels where the alkylation zone is housed. The transalkylation zone can have one or more catalyst beds containing the same or different transalkylation catalysts or catalyst mixtures.

Figure 4:
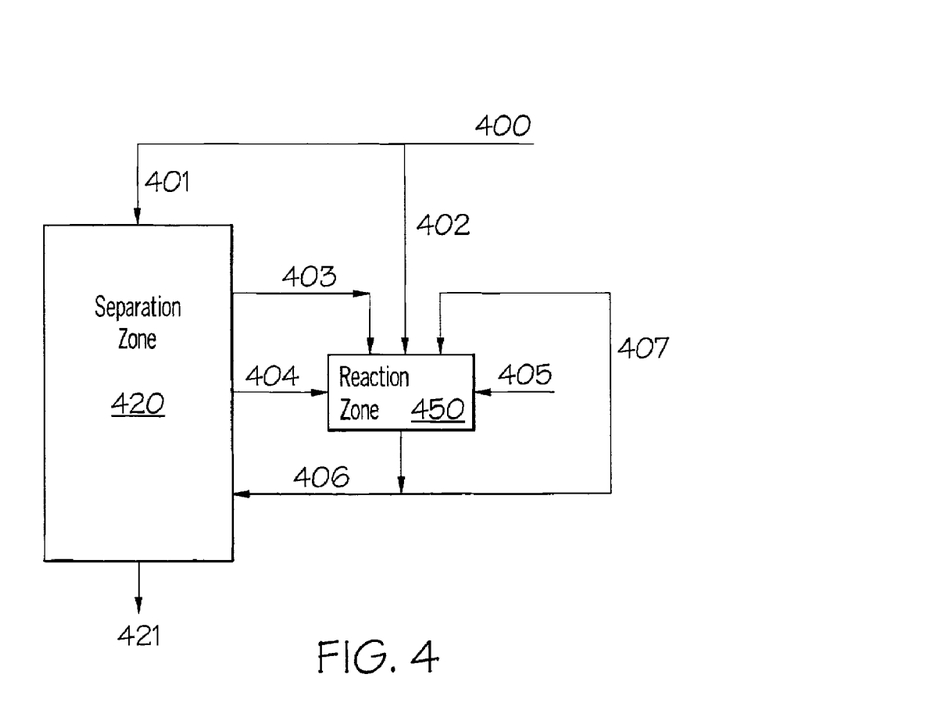
FIG. 4 is a schematic representation of a second embodiment of the present invention wherein the reaction section comprises a combined alkylation-transalkylation zone.

A second embodiment of the present invention wherein the reaction section comprises a combined alkylation-transalkylation zone is illustrated schematically in FIG. 4. As shown in FIG. 4, the fresh aromatics feed 400 can enter the process either via line 401 into separation zone 420 or via line 402 into the combined reaction zone 450. The aromatics recovered from separation zone 420 is introduced into combined reaction zone 450 via line 403, and the fresh olefin feed enters the process via line 405 into the combined reaction zone 450. The polyalkylaromatic product recovered in separation zone 420 is introduced into the combined reaction zone 450 via line 404. The effluent from the combined reaction zone 450 is sent to separation zone 420 via line 406. The monoalkylated product is removed in the separation zone via line 421.

As seen in FIG. 4, the second embodiment of the present invention comprises the following process steps:

(a) introducing into a combined reaction zone by three or more individual component feeds or one or more at least partly combined feeds, a reaction mixture comprising fresh and recycle aromatics, fresh olefin, and recycled polyalkylaromatics, wherein the molar ratio of aromatics to olefin in the mixture is in excess of 1:1, and the weight ratio of aromatics to recycle polyalkylaromatics is in excess of 0.2:1, and also wherein the combined reaction zone includes a suitable catalyst or catalyst mixture capable of catalyzing both alkylation and transalkylation;

(b) contacting the reaction mixture with the catalyst(s) under sufficient reaction conditions to react essentially all the olefins in the reaction mixture to monoalkylated aromatics and polyalkylated aromatics, and to react the aromatics and the polyalkylaromatics in the reaction mixture to produce additional monoalkylaromatics, to produce an effluent from the combined reaction zone comprising monoalkylated aromatics, polyalkylated aromatics and the unreacted aromatics, further wherein the amount of polyalkylaromatics in the effluent is about the same as that in the total feed to the reaction zone; and, (c) introducing the reaction zone effluent into a separation zone wherein the desired monoalkylated aromatics product is isolated and recovered and the unreacted aromatics and polyalkylated aromatics are recovered and recycled.

The combined reaction step of this second embodiment of the present invention may be carried out in at least partial liquid phase at temperatures between about 150° F. (66° C.) and 900° F. (482° C.) and at pressures between about 150 (1034 kPAg) and 2000 psig (13788 kPAg), over one or more beds of suitable catalyst(s) comprising at least one solid acid oxide selected from the group consisting of: zeolite beta, zeolite Y, ZSM-5, PSH-3, ITQ-2, ZSM-12, MCM-22, MCM-36, MCM-49, MCM-56, MCM-58, MCM-68, faujasite, mordenite, porous crystalline magnesium silicates, and tungstate modified zirconia. The reaction of aromatics and olefin to produce the monoalkylaromatics and polyalkyl-aromatics, and the reaction of aromatics and polyalkylaromatics to produce additional monoalkylaromatics, is believed to take place simultaneously over at least one catalyst bed.

The combined reaction zone of this embodiment of the present invention can be housed in one or more vessels. Each reaction vessel may comprise one or more catalyst beds of the same or different catalysts or mixtures of suitable catalysts. Olefin feed is introduced into at least one of the catalyst beds, but not necessarily into each of the beds if there is more than one. Part of the total effluent from the combined reaction zone may be recycled back to some or all of the catalyst beds, with or without cooling, for temperature control purposes.

One variation of this embodiment of the invention can have fresh and recycle aromatics, effluent recycle, and recycle polyalkylaromatics (but not the olefin feed) introduced to the first of a plurality of sequential catalyst beds. In such embodiment, olefin feed can then be introduced into some or all of the downstream catalyst beds.

The overall molar ratio of aromatics to olefin fed to the reaction zone is in excess of 1:1, preferably between about 1:1 and 20:1, more preferably about 2:1. The olefin fed to the reaction zone is essentially completely reacted. The overall weight ratio of aromatics to polyalkylaromatics fed to the alkylation zone in excess of 0.2:1, preferably is between about 0.2:1 and 20:1, more preferably about 2:1.

The following examples will further illustrate the practice and advantages of the present invention.

EXAMPLE 1

For production of cumene, computer simulations were carried out to determine the required total benzene circulation at different alkylator feed benzene to propylene molar ratios. The following four reactor configurations were considered: (1) the conventional parallel alkylator and transalkylator reactor configuration (FIG. 1); (2) the transalkylator-alkylator cascaded configuration provided in U.S. Pat. Nos. 5,902,917 (Collins) and 6,096,935 (Schulz) (FIG. 2); (3) the configuration of the first embodiment of this invention—alkylator and transalkylator in series configuration (FIG. 3); and, (4) the configuration of the second embodiment of this invention—combined alkylation/transalkylation zone (FIG. 4).

Figure 5:
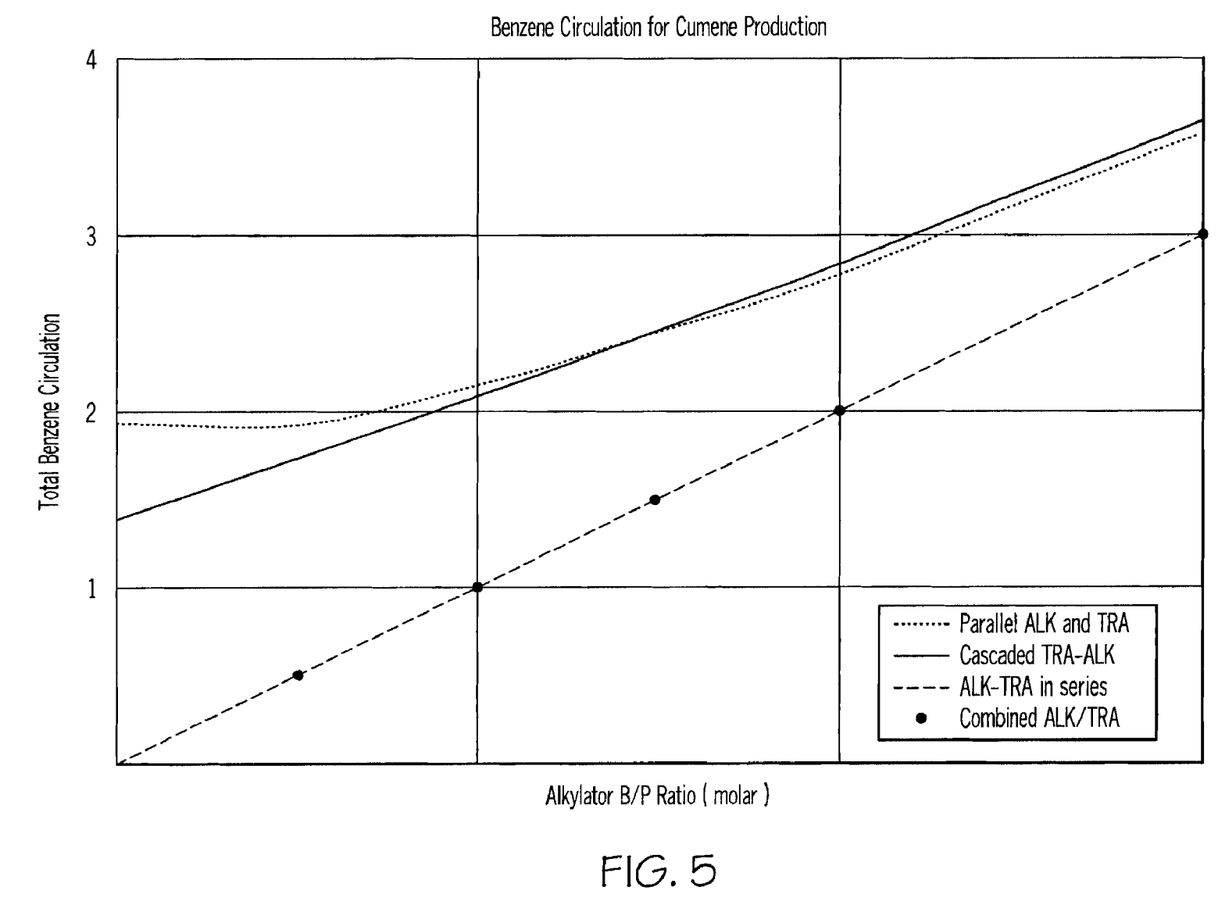
FIG. 5 is a graph comparing total benzene circulation for production of cumene at varying alkylator benzene/propylene feed ratios for the prior art reactor configurations of FIGS. 1 and 2 with those for the reactor configurations of the present invention, namely FIGS. 3 and 4.

The weight ratio of benzene to polyisopropylbenzenes in the transalkylator feed in the first two reactor configurations considered above was 2. As shown in FIG. 5, the two reactor configurations provided in the present invention require significantly less benzene circulation than either the conventional parallel alkylator-transalkylator configuration (parallel ALK and TRA—dotted line) or the cascaded transalkylator-alkylator configuration (cascaded TRA-ALK—solid line), thereby confirming the superiority of the reactor embodiments of this invention (ALK-TRA in series configuration—dashed line) and (Combined ALK/TRA configuration—bold face dots).

EXAMPLE 2

An alkylation reactor and transalkylation reactor were configured in a series configuration in accordance with FIG. 3 of the present invention. An MCM-22 type catalyst provided by ExxonMobil Chemical Company (identified as MC-1124) was loaded into the alkylation reactor. The amount of the catalyst loaded in the rector was 60 grams. A feed comprising 30 grams per hour (0.71 moles/hr) of propylene and 110 grams per hour (1.41 moles/hr) of benzene was introduced into the alkylation reactor. The alkylation reactor inlet temperature was maintained at 262° F. (128° C.). The alkylation reactor outlet temperature was maintained at about 284° F. (140° C.) by recycling part of the alkylation reactor effluent back to the inlet of the alkylation reactor. The alkylation reactor pressure was maintained at about 370 psig (2551 kPAg).

Another MCM-22 type catalyst provided by ExxonMobil Chemical Company (identified as MC-1122) was loaded into the transalkylation reactor. The amount of the catalyst loaded in the reactor was 15 grams. A feed comprising 17 grams per hour of alkylator effluent from the above alkylation reactor and 4 grams per hour of diisopropylbenzenes recovered from alkylator effluent was introduced into the transalkylation reactor. No fresh benzene was fed to the transalkylator zone.) The transalkylation reactor inlet temperature was maintained at 320° F. (160° C.), and the transalkylation reactor pressure was maintained at about 370 psig (2551 kPAg). A comparison of diisopropylbenzenes in the alkylator effluent, the recovered diisopropylbenzenes, and the transalkylator effluent, as listed in TABLE 1 below, shows that substantially all of the diisopropylbenzene byproduct produced in the alkylator were reacted to monoalkylaromatic compound in the transalkylator.

TABLE 1

| Compound | In alkylator effluent, g/hr | In recovered DIPB, g/hr | In transalkylator effluent g/hr |
| --- | --- | --- | --- |
| Benzene | 8.4 | 0.0 | 7.4 |
| Cumene | 6.9 | 0.0 | 9.3 |
| Diisopropylbenzenes | 1.3 | 4.0 | 4.0 |

EXAMPLE 3

A combined alkylation-transalkylation reactor was configured in accordance with FIG. 4 of the present invention. An MCM-22 type catalyst provided by ExxonMobil Chemical Company (identified as MC-1571) was loaded into the combined reactor. The amount of the catalyst loaded in the combined rector was 60 grams. A feed comprising 30 grams per hour of propylene (0.71 moles/hr), 101 grams per hour of benzene (1.29 moles/hr), and 59 grams per hour of recycle diisopropylbenzenes was introduced into the combined reactor. The recycle diisopropyl-benzenes was of about 93% purity. The combined reactor inlet temperature was maintained at 365° F. (171° C.). The combined reactor outlet temperature was maintained at 361° F. (183° C.) by recycling part of the combined reactor effluent back to the combined reactor inlet. The combined reactor pressure was maintained at about 370 psig (2551 kPAg). A comparison of the combined reactor feed and effluent listed in TABLE 2 below indicates that the combined reactor produced 78 grams per hour (0.65 moles/hr) of cumene without producing essentially any additional diisopropylbenzene byproduct in this experiment.

TABLE 2

| Compound | In feed, g/hr | In effluent, g/hr |
| --- | --- | --- |
| Propylene | 30 | 0 |
| Benzene | 101 | 51 |
| Cumene | 0 | 78 |
| Diisopropylbenzenes | 55 | 55 |
| Others | 4 | 6 |

It will be apparent to those skilled in the art that other changes and modifications may be made in the above-described apparatus and processes for producing alkylaromatic compounds without departing from the scope of the invention herein, and it is intended that all matter contained in the above description shall be interpreted in an illustrative and not a limiting sense.

We claim:

1. A process for producing a monoalkylated aromatic product in a combined reactor zone having a plurality of sequential catalyst beds, said process comprising the following process steps:
   (a) introducing into a first catalyst bed of the combined reaction zone a first reaction mixture comprising fresh and recycle aromatics, effluent recycle, and recycle polyalkylaromatics but not an olefin feed;
   (b) introducing into a second catalyst bed of the combined reaction zone by three or more individual component feeds or one or more at least partly combined feeds, a reaction mixture comprising fresh and recycle aromatics, fresh olefin, and recycled polyalkylated aromatics, wherein the overall molar ratio of aromatics to olefin in the mixture is between 1:1 to 20:1, and the weight ratio of aromatics to recycled polyalkylated aromatics is in excess of 0.2:1, and also wherein the first and second catalyst beds of the combined reaction zone include a suitable catalyst or catalyst mixture capable of catalyzing both alkylation and transalkylation;
   (c) contacting the reaction mixtures with the catalyst(s) under sufficient reaction conditions to react essentially all the olefins in the reaction mixture to monoalkylated aromatics and polyalkylated aromatics, and to react the aromatics and the recycled polyalkylated aromatics in the reaction mixture to produce additional monoalkylaromatics, to produce an effluent from the combined reaction zone comprising monoalkylated aromatics, polyalkylated aromatics and the unreacted aromatics, and,
   (d) introducing the reaction zone effluent into a separation zone wherein the desired monoalkylated aromatics product is isolated and recovered and the unreacted aromatics and polyalkylated aromatics are recovered and recycled.

2. The process according to claim 1 wherein the reaction of step (c) is carried out in at least partial liquid phase at temperatures between 150° F. and 900° F. and at pressures between 150 psig and 2000 psig.

3. The process according to claim 1 wherein the catalyst or catalyst mixture comprises at least one solid acid oxide selected from the group consisting of zeolite beta, zeolite Y, ZSM-5, PSH-3, TTQ-2, ZSM-12, MCM-22, MCM-36, MCM-49, MCM-56, MCM-58, MCM-68, faujasite, mordenite, porous crystalline magnesium silicates, tungstate modified zirconia and mixtures thereof.

4. The process of claim 1 wherein the aromatics to polyalkylaromatics fed to the reaction zone is between 0.2:1 and 20:1 and such that the olefin fed to the reaction zone is essentially completed reacted with the aromatics feed.

5. The process of claim 1 wherein the aromatics are benzene.

6. The process of claim 5 wherein the olefin are selected from the group consisting of ethylene and propylene.

7. The process of claim 1 wherein the monoalkylaromatics are selected from the group of ethylbenzene and cumene.

8. The process of claim 1 wherein the polyalkylaromatics are selected from polyethylbenzene and polyisopropylbenzene.

9. The process of claim 1, wherein the amount of polyalkylaromatics in the effluent is about the same as that in the total feed to the reaction zone.

10. The process of claim 1, wherein essentially no additional polyalkylaromatics byproduct is produced.

11. The process of claim 3, wherein the at least one solid acid oxide of the catalyst or catalyst mixture are the same or different.

* * * * *